United States Patent
Chen et al.

(10) Patent No.: US 7,183,074 B2
(45) Date of Patent: Feb. 27, 2007

(54) GAS DUAL-DYNAMIC SOLID STATE FERMENTATION TECHNIQUE AND APPARATUS

(75) Inventors: Hongzhang Chen, Beijing (CN); Zuohu Li, Beijing (CN)

(73) Assignee: Institute of Process Engineering, Chinese Academy of Sciences, Beijing (CN)

( * ) Notice: Subject to any disclaimer, the term of this patent is extended or adjusted under 35 U.S.C. 154(b) by 597 days.

(21) Appl. No.: 10/341,956

(22) Filed: Jan. 14, 2003

(65) Prior Publication Data
US 2003/0138943 A1    Jul. 24, 2003

(30) Foreign Application Priority Data
Jan. 22, 2002   (CN)  ............................ 2002 1 00176

(51) Int. Cl.
*C12M 1/14*      (2006.01)
(52) U.S. Cl. ....................... 435/41; 435/93; 435/297.1; 435/819
(58) Field of Classification Search ...................... None
See application file for complete search history.

(56) References Cited

U.S. PATENT DOCUMENTS

| | | | |
|---|---|---|---|
| 621,014 A | * | 3/1899 | Bachmann .................... 435/93 |
| 6,197,573 B1 | * | 3/2001 | Suryanarayan et al. .. 435/286.7 |

FOREIGN PATENT DOCUMENTS

| | | |
|---|---|---|
| CN | 1093749 | 10/1994 |
| CN | 1114686 | 1/1996 |
| CN | 1120583 | 4/1996 |
| CN | 1142533 | 2/1997 |
| DE | 298 425 | 2/1992 |
| SU | 1763489 | 9/1992 |

* cited by examiner

*Primary Examiner*—David Redding
(74) *Attorney, Agent, or Firm*—McDonnell Boehnen Hulbert & Berghoff LLP

(57) ABSTRACT

The gas dual-dynamic solid state fermentation technique consists of placing the solid materials to be fermented in an air environment with pulsating pressure and cyclic flow to carry out fermentation, the fermentation apparatus comprises a horizontal cylindrical tank with a quick door mechanism, in the tank are axially disposed rectangular spacer barrels of square cross-section constructed by four baffles, in the space between baffles and the tank wall are provided cooler tubes in parallel with the baffles, in the middle of the spacer barrels are provided vertically many sets of cooler tubes, on the lower baffles in the tank is provided axially an fixed track, on which are movable tray racks that can roll on the track, the tray racks having thereon a plurality of layers of trays, at the rear of the tank is provided a centrifugal blowers for forcing gas cycling in the tank. The inventive technique and apparatus allows microbial pure cultivation, is easy for scaling up and high in fermentation virulence titre and produce no pollution. It is useful for fermentation production of biological pesticides, enzyme preparations, agricultural antibiotics and unicell albumen.

8 Claims, 2 Drawing Sheets

GAS DUAL-DYNAMIC SOLID STATE FERMENTATION TECHNIQUE AND APPARATUS

FIELD OF THE INVENTION

The present invention relates to the field of fermentation techniques, and particularly to a gas dual-dynamic solid state fermentation technique and apparatus.

BACKGROUND OF THE INVENTION

Since penicillin discovered by Fleming was successfully put into industrial production through the cooperation between microbiologists and chemical engineers in 1945, Submerged fermentation technique has opened a modem fermentation industry. Solid state fermentation has not fulfilled the requirement of modem fermentation industry and has thus been ignored because it has no engineering means to solve the problems such as transportation, agitation, oxygen supply and control of temperature, humidity and pH. The key point is there has not been a good solid state fermentor meeting the requirements of modem fermentation industry, which remains a world-wide difficulty.

The strict requirement on microbe pure cultivation and large scale production imposed by modem fermentation industry makes liquid submerged fermentation occupy a dominating position. Solid state fermentation technology has been regarded as old and backward because its process and equipment are subject to bacteria pollution, its fermentation conditions are difficult to control and its industrial scaling up is difficult. Solid state fermentation, however, has many advantages, for example, simple and short flow process, wide availability of raw materials, low energy consumption, low cost and no pollution; it is, therefore, very attractive and potential in the development of bioreactors. In order to change the backwardness of solid state fermentation industry, for half a century, especially since the appearance of biochemical engineering in the seventies of the 20th century, there has been no lack of people who attempted to solve this difficult problem by proposing various means, B. K. Lonsane summarized them into nine types (1) drum type, (2) wooden box type, (3)capped plate type, (4) vertical cultivation box type (5) inclined culturing box type, (6) tray type, (7)belt conveyor type, (8) cylinder type (9) mixed type, K. E. Aidou divided the solid state fermentation apparatus into ten types, similar with those proposed by B. K. Lonsane. They can be summarized into two categories, namely static and dynamic according to the state of culture medium. Static state means motionless culture medium, which makes mass transfer, heat transfer, oxygen supply and control of temperature, humidity and pH difficult. Dynamic state means that the culture medium is in intermittent and continuous motion, which significantly improves mass transfer, heat transfer and oxygen supply, but the mechanical parts used are unfavorable to aseptic operation, energy consumption on material agitating is high, mycelia are likely to be damaged, and engineering scaling up is difficult.

On one hand, people try to improve the traditional solid state fermentors, such as bend trays, bend boxes and bend pools, mainly mechanizing physical labor involved and strengthening ventilation. On the other hand, people actively develop closed type solid state fermentor with mechanical agitation suitable for microbe pure cultivation, among others, the most studied is the drum type, and there are rotating tray or rotating rake type, belt conveyor type, mechanical lifting type and the like. Because of the reasons such as complicated driving mechanism, no easy strict sealing and dead space being not readily cleaned, solid state fermentors of such types have not met the practical requirement imposed on pure cultivation and industrial scaling up by modem fermentation industry.

The solid state fermentors used in production nowadays are still the traditional tray type and deep layer ventilation pond types, as well as the practice of placing culture medium pressed as cakes or square bricks in rooms. A larger scale method uses tunnel kiln continuous tray fermentation. All the types described above are static and used in the production process of natural fermentation. From the view point of the "three transfers and one reactor" chemical engineering theory, the direction of development should be dynamic fermators for intensifying mass and heat transfer. Dynamic fermentation reactors of closed type have, therefore, been the hot point in research in China and other countries. Particularly, drum type solid state fermentation reactors are reported in many literatures to have gone into an industrial pilot test stage. They did not endure tests of long time production because of being difficult to prevent pollution with miscellaneous bacteria. Closed dynamic fermentation reactors of other types are still limited to being in laboratory research.

BRIEF SUMMARY OF THE INVENTION

One object of the invention is to solve the problems of easy pollution with miscellaneous microorganisms and difficulty in mass and heat transfer and scaling up in the existing solid state fermentation techniques and provide a gas dual-dynamic solid state fermentation technique that is useful for pure cultivation, fast in transfer rate and easy to scale up.

Another object is to solve the problems of easy pollution with miscellaneous microorganisms and difficulties in mass and heat transfer and scaling up in the existing solid state fermentation techniques and provide a gas dual-dynamic solid state fermentation apparatus that is useful for pure cultivation, fast in transfer rate and easy to scale up.

DETAILED DESCRIPTION OF THE INVENTION

Figure 1:
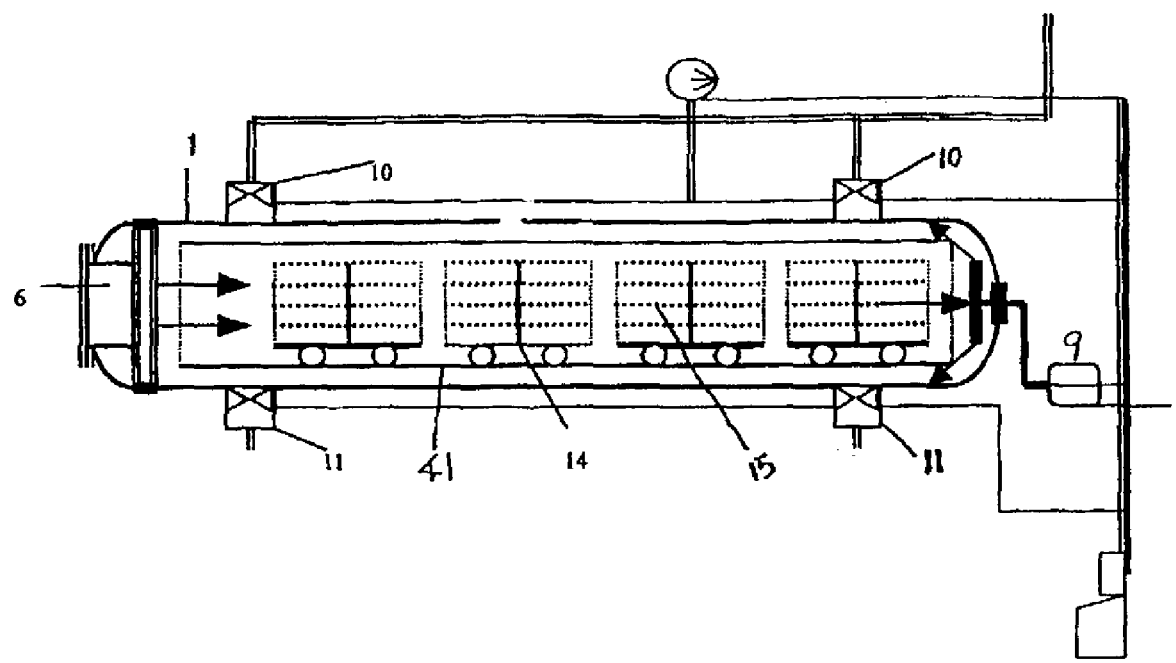
FIG. 1 is a schematic view of the embodiment structure of the invention.
Figure 2:
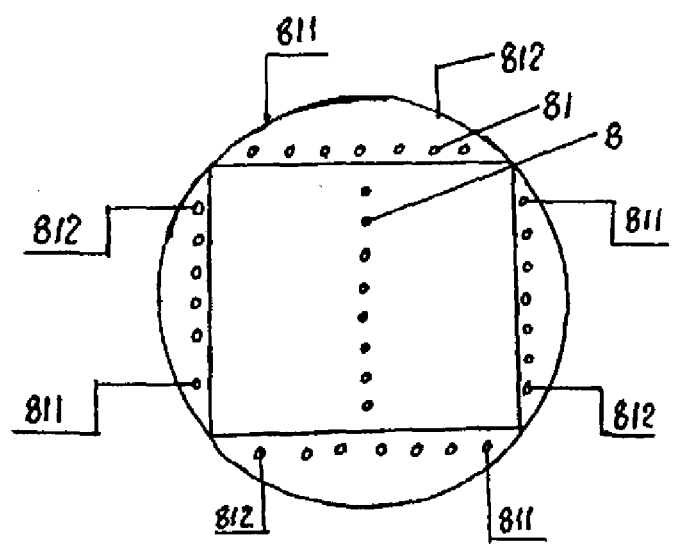
FIG. 2 is a longitudinal schematic sectional view of rectangular spacer barrel of the invention.
Figure 3:
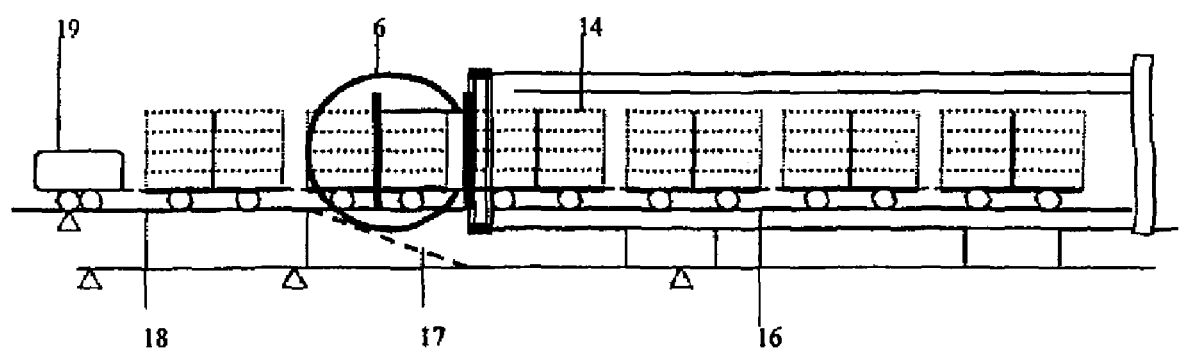
FIG. 3 is the schematic view of the connection of the inside fixed track 16, the outside movable track 17 and the outside fixed track 18.
Figure 4:
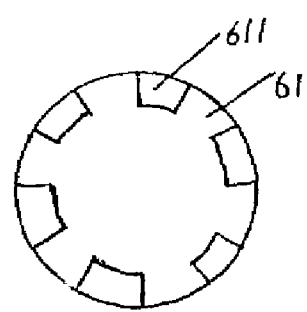
FIG. 4 is a schematic view of the lobe structure of the front end of the tank.
Figure 5:
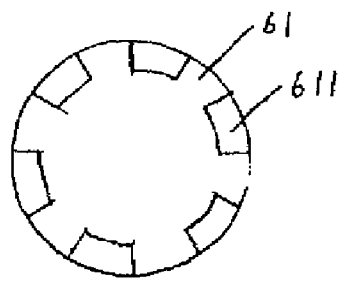
FIG. 5 is a schematic view of the lobe structure of the tank cover.

There is provided a gas dual-dynamic solid state fermentation technique, characterized in that the solid materials to be fermented are placed in a dual-dynamic air environment, that is, an air environment with pulsating pressure and cyclic flow, to undergo solid state fermentation. The pressure pulsation is as follows: germ-free air is injected into a fermentor through an electromagnetic inlet value mounted on the tank body to control the pressure in the tank within the range from 1.5 kg/cm$^2$ to 3.5 kg/cm$^2$; after the pressure reaches the set value, the electromagnetic inlet value is closed and the pressure is maintained for 1 to 5 minutes; an electromagnetic outlet value mounted on the tank body is closed to let the air flow out, namely to depressurize the tank, until the pressure within the tank reaches 0.1 to 0.5 kg/cm$^2$; the outlet value is closed and the pressure is maintained for 10 to 60 seconds; after that the pressurization and depressurization processes are repeated by opening and closing the two valves alternately. The solid state fermentation of materials is carried out in this way in a dual-dynamic control of air with pulsating pressure and cyclic flow.

The gas dual-dynamic solid state fermentation apparatus of this invention comprises a horizontal cylindrical tank 1, at the front end of the tank 1 there is a quick door opening mechanism 6 for quick opening or closing the tank door; at both two ends of upper tank wall are respectively mounted gas mounted gas inlet pipes controlled by gas inlet valves 10; and at both two ends of lower tank wall are respectively mounted gas outlet pipes controlled by gas outlet valves 11. The apparatus is characterized in that: in the tank 1 there are axially disposed rectangular spacer barrels of square cross-section constructed by four baffles 41; in the space between baffles 41 and the tank wall there are provided cooler tubes 81 in parallel with the baffles, with condensed water outlet tubes 811 connected at one end of the cooler tubes 81 and condensed water inlet tubes 812 at the other end of the cooler tubes 81; in the middle of the rectangular spacer barrels there are provided vertically a plurality of sets of cooler tubes 8 with each set of cooler tubes 8 having the respective condensed water outlet tubes and inlet tubes; on the dower baffles 41 in the tank 1 there is provided axially an inside fixed track 16, on which are movable tray racks 14 that can roll on the track 16, the movable tray racks 14 having thereon a plurality of horizontal trays 15 for placement of solid culture medium and being of one row or two rows; on the rear tank wall there is connected a centrifugal blower 9 for forcing gas cycles in the tank; the said quick door mechanism 6 is staggered lobes construction: on the front end of the tank and the surface of the tank cover opposite to the said end are respectively provided concave lobes 61 and convex lobes 611 staggered to each other and closely engaged, with the tank cover driven by a motor and lobe engaged with the front end of the tank; the said axially positioned inside fixed track 16 is connected with an outside movable track 17 which is outside the tank, and the other end of the outside movable track 17 is connected with an outside fixed track 18 and a mechanical tractor 19 on the outside fixed track 18 pulls the movable tray racks 14 into and out of the solid state fermentor.

The fundamental feature of this invention firstly lies in periodically pulsating the gas-phased pressure in the solid state fermentor with the period, amplitude and wave form of pulsation changing with the different fermentation material and fermentation duration. Secondly, in the gas dual-dynamic solid state fermentor there are provided cyclic ventilation ducts and many sets of cooler tubes, and the air in the tank is forced to flow through the material and cooler tubes successively, forcibly carrying away the heat in the material and forcibly causing the hot air to undergo heat exchange with the cooling coil, lowering the temperature of the material being fermented, and assuring the homogenization and adjustability of fermentation temperature and humidity. Such a gas dual-dynamic method and apparatus has triple effects: (1) the microbial metabolism is accelerated; (2) the transfer in and out through cell walls of nutrients and products of metabolism is accelerated; (3) the mode of mass and heat transfer between the gas in the space among the particles in solid state culture medium stack layer and the bulk gas phase is changed to convective diffusion from molecular diffusion.

The dissipation of heat and carbon dioxide generated by microbial metabolism in solid state culture medium stack layers, in traditional solid state stack fermentation, is accomplished mainly by using thin layer, mechanical ruffling or air blowing from below. Thin layer fermentation depends on shortening the diffusion path of static gas molecules in interparticle space for heat dissipation, while mechanical ruffling or air blowing from below depends on changing molecular diffusion to convective diffusion but bringing heavy damage to thalli. It is also possible to change molecular diffusion to convective diffusion by use of gas dual-dynamic operation. Here, gas will flow into interparticle space when the pressure in bulk gas phase is increased until the pressure is equilibrated. When the pressure in bulk gas phase is lowered, the gas in interparticle space will flow into the bulk gas until the pressure is equilibrated at a lower pressure; meanwhile, forcing the air in the tank to flow successively through the material and cooler tubes ensures that the temperature and humidity of fermentation be uniform and adjustable.

For example, for cellulase fermentation, the enzymatic activity of the product by gas dual-dynamic fermentation method is 2 to 3 times that by constant pressure fermentation method. Fermentation time is generally shortened to two-thirds, for example, for B.t fermentation, it is 2 days during varying pressure process against 3 days during constant pressure process. For muscardine or green muscardine fungus, 5 days against 7 days. For ovoflavin, fermentation time can be shortened from 12 days to 7 days. The number of living spores by muscardine fermentation is up to $8*10^{10}$/g from the experimental results, generally more than $5*10^{10}$/g.

The invention is characterized in the following:

1 The use of thin layer, gas dual-dynamic process and cyclic blowers meets the requirement on mass and heat transfer without any device for mechanical ruffling the solid layers.

2 The construction of said reactor is simple, easy to seal and convenient to scale up because no solid ruffling mechanism and its drive are involved.

3 The reactor is a vessel capable of being pressurized, so it can be sterilized strictly by steam at high pressure in empty state or with materials in. There is no dead space in it, so it is convenient to clean.

4. Germ-free compressed air is used to supply oxygen and, therefore, the reactor is in a positive pressure state during fermentation, strictly satisfying the requirement for solid state cultivation.

5. The gas dual-dynamic process has the function of improving microbial metabolism, intensifying the mass transfer in and out of cells, reducing the feed-back suppression of products of metabolism, whereby shortening fermentation period and increasing conversion.

6. The ring structure of the reactor in combination with cyclic blowers allows the temperature and humidity within the reactor to be uniform.

7. The provision of cooler tube in the reactor in addition to the use of blowers forces the air in the reactor to flow through solid materials and cooler tube successively to decrease the material temperature and facilitate the control of the temperature and humidity in the reactor.

8. The period, amplitude and wave form of gas dual-dynamic process are automatically controlled in real time, the control being on line optimum control by means of computer according to the requirements of oxygen supply and heat requirement during the fermentation process.

The substantial difference of this invention from traditional solid state fermentation lies in the following:

The implementation of pure cultivation in strict sense and production on an industrial scale;

A rise of fermentation virulence titre by 4–6 times due to cyclic stimulation;

Controllability of temperature, humidity and pH during fermentation;

Increasing rather than decreasing in virulence titre after vacuum freeze drying;

No pollution to environment;

Increase in equipment investment as compared to traditional fermentation, but far more decrease as compared to deep liquid layer fermentation.

Such a solid state fermentation technique fundamentally changes the prevalent concept that solid state fermentation is an old and backward production process because it is more advanced than deep liquid layer fermentation technique. The existing textbooks on fermentation engineering and biochemical engineering are to be rewritten. Fermentation technology history has gone through a spiral step.

This gas dual-dynamic solid state fermentation technique, being a new type solid state fermentation technique different from the submerged fermentation technique, will have a wide use and a popularization significance. It accomplishes a dual object required by modem fermentation engineering, that is, technological pure cultivation and industrialization on a large engineering scale. This advanced high technology is creative internationally since it has been accepted as very difficult internationally for a long time.

The applicator of this invention has been persisting in the study of solid state fermentation technique and apparatus since 1984. In 1999, he developed a gas dual-dynamic solid state fermentation technique and apparatus of this invention guided by the "four transfers and one reactor" nonlinear theory and the design principle that "external cyclic stimulation intensifies biological reactions and the mass transfer rate inside and outside cells" with the normal force as the drive of the principle. It was tested from a 0.5 liter lab test to an 800 liters pilot-plant test, again to a 25,000 liters and 70,000 liters industrial scale test. An exemplary solid state fermentation plant has been established for pure cultivation of Dipel wettable powder on a large scale, exhibiting economic targets better than deep liquid layer fermentation. It is a breakthrough in solid state fermentation technology in China and probably in fundamental theory of the new subject "biological reaction engineering as well as in the research of Dipel industrialization.

The operation procedure is as follows: Firstly, carry on sterilization treatment of the empty tank (including movable tray rack); then cool it, pass in germ-free air, open the quick door by its mechanism, pull out the movable tray rack, and place the cultured solid state fermentation medium layer on the trays; After that immediately push the tray rack into the tank body of fermentation apparatus and close the quick door, adjust the temperature and humidity in the tank body and carry out gas dual-dynamic control; carry out vacuum freeze drying by means of heating system at the end of fermentation.

Operation Method

The main operation is to apply periodical pulsation to the germ-free air in the tank body with the pressure change in the tank body as shown in FIG. 1; the pressure periodically changes between peak pressure and low-pressure by charging and discharging the germ-free air; the time of a cycle consists of the time of air charging, the time of stabilization at peak pressure, the time of air discharging and the time of stabilization at low pressure, the pressure in the tank always being positive. The peak pressure is generally 1.5 to 3.5 $kg/cm^2$ and the low pressure is generally 0.1 to 0.5 $kg/cm^2$. The air charging time is relatively long, with the pressure curve rising up gently for 1 to 5 minutes depending on the capacity of air source. The air discharging time is required to be as short as possible, generally 1 minute, and the pressure decrease rate must be large especially in the first ten seconds so that the gas between wet substratum solid particles abruptly expands and the material layer is loosened. The peak pressure stabilization time and the low pressure stabilization time can be controlled with the former longer than the latter and both changing with fermentation time. The frequency of pressure change during the exponential pressure rise is high while those during the pressure delay and stabilization are small. The time of one cycle is generally 15 to 150 minutes. Automatic control is easy because of simple operation of tank pressure.

In the drawings:

| | | |
|---|---|---|
| Tank 1 | Quick door mechanism 6 | Gas inlet valve 10 |
| Gas outlet valve 11 | Baffle 41 | Cooler tubes 81 |
| Condensed water outlet valve 811 | Condensed water inlet Tube 812 | Cooler tubes 8 |
| Movable tray rack 14 | Tray 15 | Centrifugal blower 9 |
| Outside movable track 17 | Outside fixed track 18 | Mechanical tractor 19 |
| Concave lobe 61 | Convex lobe 611 | Inside fixed tractor track 16 |

Now the invention is further described in connection with the drawings and examples.

EXAMPLE 1 the production of B.t biological pesticide wettable powder using the solid state fermentation apparatus shown in FIG. 1 and the method according to the invention.

As seen in FIG. 1, the gas dual-dynamic solid state fermentation apparatus of this invention comprises a horizontal cylindrical tank 1, at the front end of the tank 1 there is a quick door mechanism 6 for quickly opening or closing the tank door; at both two ends of upper tank wall are respectively mounted gas inlet pipes controlled by gas inlet valves 10; and at both two ends of lower tank wall are respectively mounted gas outlet pipes controlled by gas outlet valves 11. The apparatus is characterized in that: in the tank 1 there are axially disposed rectangular spacer barrels of square cross-section constructed by four baffles 41; in the space between baffles 41 and the tank wall there are provided cooler tubes 81 in parallel with the baffles, with condensed water outlet tubes 811 connected to one end of the cooler tubes 81 and condensed water inlet tubes 812 to the other end of the cooler tubes 81; in the middle of the rectangular spacer barrels there are provided a plurality of sets of cooler tubes 8 with each set of cooler tubes 8 having the respective condensed water outlet tubes and inlet tubes, the cooler tubes 8 arranged vertically within and along the longitudinal axis of the rectangular spacer barrel such that cooler tubes 8 are located in the space between the horizontal trays; on the lower baffles 41 in the tank 1 there is provided axially an inside fixed track 16, on which are movable tray racks 14 that can roll on the track 16, the movable tray racks 14 having thereon a plurality of horizontal trays 15 for placement of solid culture medium and being of one row or two rows; on the rear tank wall there is connected a centrifugal blower 9 for forcing gas to cycle in the tank; the said quick door mechanism 6 is of staggered lobes construction: on the front end of the tank and the surface of the tank cover opposite to the said end are respectively provided alternating concave lobes 61 and convex lobes 611 wherein a concave lobe 61 located on the tank cover is complementary to a convex lobe 611 located on the tank surface and wherein a convex lobe 611 located on the tank cover is complementary to a concave lobe 61 located on the tank cover, with the tank cover driven by a motor and lobe staggeredly engaged with the front end of the tank; the said axially positioned inside fixed track 16 is connected with an outside movable track 17 which is outside the tank, with the other end of the outside movable track 17 is connected with an outside fixed track 18 and a mechanical tractor 19 on the outside fixed track 18 pulls the movable tray racks 14 into and out of the solid state fermentor.

The microorganisms species used in this example: Dipel (B.t Var Kurstaki); fermentation medium: bran, cotton seed cake powder, corn flour, rice bran, corn paste, quick lime, containing 51% to 60% water; fermentation condition: 30° C., 30% humidity; pressure pulsation period: 10 to 60 minutes; pressure amplitude: 0.5–30 $kg/cm^2$; wave form: rapid depressurizing and pressurizing.

Comparative solid state fermentation tests on the above materials were made using gas dual-dynamic solid state fermentation technique, flask fermentation technique and porcelain tray fermentation technique according to this invention.

The procedure of the inventive gas dual-dynamic solid state fermentation is as follows: the solid materials to be fermented are placed in an air environment with pulsating pressure and cyclic flow to undergo solid state fermentation. The pressure pulsation is done as follows: germ-free air is injected into a fermentor through an electromagnetic inlet valve mounted on the tank body to control the pressure in the tank within the range from 1.5 to 3.5 $kg/cm^2$; after the pressure reaches the set value, the electromagnetic valve is closed and the pressure is maintained for 1 to 5 minutes; an electromagnetic outlet valve mounted on the tank body is closed to let air flow out, namely to depressurize the tank, until the pressure within the tank reaches 0.1 to 0.5 $kg/cm^2$; the outlet valve is closed and the pressure is maintained for 10 to 60 seconds; after that the pressurization and depressurization processes are repeated by opening and closing the two valves alternately. The solid state fermentation of materials is carried out in this way in a gas dual-dynamic control of air in pressure pulsation and cyclic flow.

The flask and porcelain tray fermentation procedures used are conventional and thus is not described here.

The pesticide Dipel *Bacillus thuringiensis*(B.t) is considered to be the most effective and representative microbial preparation belonging to the biological control field. It is used to kill the insects with basic stomach of over 500 species of 10 orders such as *lepidoptera, diptera, coleopter* and *orthoptera*, and leads to very good results of petis prevention and control with respect to vegetables, fruit trees, cotton, tea, tobacco, forest, corn, rice, soybean and grain storage even the field of mosquitos, flies and the like. Because it has killing effect on insects with basic stomach, it does no harm to human, livestock and birds with acidic stomach, and it is not pollutant to the environment, and injurious insects are not likely to become resistant to pesticides. It is the most important microbial pesticide rapidly appearing since the eighties of the 20th century.

The World Health Organization has long verified that B.t does no harm to human, livestock, birds and fish. B.t production personnel have not found to be poisoned in China and other countries for several decades.

According to Departmental Standard of China, there are B.t products of two kinds and six specifications. One kind is emulsion with virulence titre being 2000 IU/µl, 4000IU/µl, 8000IU/µl. The other kind is wettable powder with virulence titre being 8000 IU/mg, 16000 IU/mg, 32000 IU/mg. The virulence titre of wettable powder on international market is generally 16000 IU/mg. The products in China are mostly emulsion with virulence titre being 2000 IU/µl.

During the gas dual-dynamic solid state fermentation, 55 tank batches were experimented with average virulence titre being 16000 UL/mg, the maximum reached 23000 IU/mg. As compared to the existing submerged fermentation, for the production of B.t biological pesticide wettable powder using gas dual-dynamic solid state fermentation new technology. We have reached the following feasibility conclusions:

B.t wettable powder is an environmental protection product badly needed and of peculiar significance to green food production. Since last year all provincial and municipal governments of China have released order that the use of chemical pesticides be prohibited in vegetable production, providing a turning point for the development of B.t.

The gas dual-dynamic solid state fermentation technique has been developed by us in China; it has creative importance both in China and other countries. As compared with the deep liquid layer fermentation currently used in China and other countries, the equipment investment is only one-fourth and the production cost is only two-fifth. This will lay a solid foundation for the creation and development of ecological engineering and agriculture.

The production of B.t wettable powder by submerged fermentation method in China has not been well developed. The product of this method is usually emulsion, the storage life of which is only three months while that of wettable powder is more than three years. The solid state fermentation technique will create a new situation in the industrialization of B.t wettable powder in China.

The results of comparative solid fermentation tests are listed in the following table.

| Type of fermentor | Fermentation time (hours) | Number of living spores ($10^8$/g) | Virulence titre (IU/mg) | Crystal separation (%) |
|---|---|---|---|---|
| The solid state fermentor of this invention | 42–48 | 250–400 | 12000–20000 | >80 |
| Flask (comparative) | 72 | 100–150 | 4000–6000 | 30–50 |
| Porcelain tray (comparative) | 72 | 150–200 | 6000–8000 | 50 |

EXAMPLE 2

A comparative solid state fermentation test of *Bacillus cereus* DM 423 used as microbial forage additive using the same methods and procedures as Example 1, the results are listed in the following table.

| Fermentation technique | Reactor type | Fermentation time (hours) | Number of living spores | Cost (Yuan/ton) |
|---|---|---|---|---|
| Submerged fermentation | Standard mechanical tank | 48 | 30–50 108/ml | 1500 |
| Solid state fermentation | The solid state fermentor of this invention | 48 | 200–300 108/g | 3000 |
| | Porcelain tray | 48 | 80–200 108/g | Polluted with microorganisms |

EXAMPLE 3

The solid state fermentation of "muscardine biological pesticide production" using the same method and procedure as Example 1.

Muscardine is an insect-generated fungus belonging to imperfect fungus group, which has a wide range of hosts. It does no harm to human, living stock, woods and natural enemies and does not pollute the environment. However, its pathogenicity is strong and thus one of the widely used microbial pesticides. Muscardine belongs to pathogenic bacteria of insects. It comes into the insect body through the epidermis or pores on epidermis of the insect. And thus kill it through pathogenesis. It has good pesticidal effect on leaf-eating injurious insects, especially on forest injurious insects. It has a broad market prospect. Currently, China is the biggest producing and employing country of muscardine pesticide in the world, applying it on an area of about 500,000 hectares annually. It has made an important contribution to the prevention and control of pine moth and corn snot moth's larva. In other countries, liquid fermentation is used for the production of muscardine at a high cost. In China, a shallow tray cultivation method is largely used with a small scale of production, serious pollution and products of unstable quality, and, therefore, is used seasonally by some tree farms. For the production of muscardine preparation, shallow tray solid state cultivation and liquid-solid state method are mainly used in China. The problems are complicated technology, long production cycle, high cost, unstable quality of product and the like, and the products are far from meeting the market requirement.

Employing the periodical stimulation solid state fermentor, which is a result of many years' research, to produce muscardine, it is possible to assure pure fermentation and easy scaling up of fermentation, its titre improved by 3–4 times as compared to tray cultivation. The number of living spores of muscardine fermentation is usually over $5*10^{10}/g$ from the experimental results.

What is claimed is:

1. A gas dual-dynamic solid state fermentation method characterized in that, solid materials to be fermented are placed in an air environment with pulsating pressure and cyclic flow to undergo solid state fermentation by the steps comprising:

a. injecting germ-free air into a fermentor tank through an electromagnetic inlet valve to control the pressure in the tank within the range from 1.5 to 3.5 $kg/cm^2$;
   b. closing the electromagnetic inlet valve after the tank pressure reaches a set value, and maintaining the tank under pressure for 1 to 5 minutes;
   c. opening an electromagnetic outlet valve to let air flow out of the tank until the pressure in the tank reaches 0.1 to 0.5 $kg/cm^2$;
   d. closing the electromagnetic outlet valve and maintaining the tank pressure for 10 to 60 seconds; and
   e. repeating steps a–c.

2. A gas dual-dynamic solid state fermentation method according to claim 1 further comprising providing a door and door opening mechanism at a front end of a horizontal cylindrical tank.

3. The gas dual-dynamic solid state fermentation method according to claim 2, further comprising:
   disposing a plurality of axially disposed rectangular spacer barrels, each barrel having a square cross-section formed by four baffles;
   disposing a plurality of cooler tubes running in parallel with the baffles and located in a space between the baffles and the tank inner wall, each cooler tube having a condensed water outlet and a condensed water inlet;
   disposing a plurality of cooler tube sets, each cooler tube set having a condensed water outlet and a condensed water inlet;
   locating a fixed track inside the tank between the plurality of cooler tubes and a spacer barrel baffle; and
   providing at least one tray rack moveable on the fixed track, the tray rack including a plurality of horizontal trays on which solid cultures are placed.

4. The gas dual-dynamic solid state fermentation method according to claim 3 wherein the movable tray rack has one row or two rows.

5. The gas dual-dynamic solid state fermentation method according to claim 2 wherein the quick door mechanism is a staggered lobe mechanism.

6. The gas dual-dynamic solid state fermentation method according to claim 3 wherein the axially positioned inside fixed track is connected to the first end of an outside movable track located outside the tank, and wherein a second end of the outside movable track is connected to an outside fixed track wherein a mechanical tractor pulls the movable tray racks into and out of the solid state fermenter.

7. The gas dual-dynamic solid state fermentation method according to claim 5 wherein the staggered lobe mechanism includes a plurality of alternating concave lobes and convex lobes located on the front end of the tank, each tank front end concave lobe having a complementary convex lobe located on the tank cover and each tank front end convex lobe having a complementary concave lobe located on the tank cover.

8. The gas dual-dynamic solid state fermentation method according to claim 3, including the step of providing a blower for providing air to pressurize the tank.

* * * * *